United States Patent [19]
Wang et al.

[11] Patent Number: 5,188,733
[45] Date of Patent: Feb. 23, 1993

[54] APPARATUS AND PROCESS FOR EFFECTING SEQUENTIAL PEPTIDE SYNTHESES

[75] Inventors: Zhengxin Wang, Boston; Richard A. Laursen, Newton, both of Mass.

[73] Assignee: Trustees of Boston University, Boston, Mass.

[21] Appl. No.: 841,943

[22] Filed: Feb. 26, 1992

[51] Int. Cl.⁵ .......................................... B01D 69/00
[52] U.S. Cl. ........................... 210/321.84; 210/638; 422/101
[58] Field of Search ............. 422/101, 102; 210/450, 210/323.1, 321.75, 321.84, 638

[56] References Cited
U.S. PATENT DOCUMENTS
4,797,259 1/1989 Matkovich et al. ............. 422/101

Primary Examiner—Frank Spear
Attorney, Agent, or Firm—Paul J. Cook

[57] ABSTRACT

A chemically modified membrane is positioned between a first template having a first set of holes and a second set of holes aligned with the first set of holes to define a plurality of exposed portions of the membrane in such as manner as to prevent collapse of pores in the membrane during application of a differential pressure across the membrane.

8 Claims, 3 Drawing Sheets

1

2

3

4

APPARATUS AND PROCESS FOR EFFECTING SEQUENTIAL PEPTIDE SYNTHESES

BACKGROUND OF THE INVENTION

This invention relates to an apparatus and process for effecting a plurality of sequential chemical syntheses in a plurality of reaction porous substrates.

Instrumentation for the automatic synthesis of peptides has been available since 1964, when Merrifield described the first automated solid phase peptide synthesizer. Since that time Merrifield-type peptide synthesizers employing Merrifield chemistry (Boc-protected amino acids, polystyrene based synthesis resins, deprotection with trifluoroacetic acid, cleavage of peptide from resin with hydrogen fluoride) have come into wide use. More recently, the so-called Fmoc method of synthesis, Atherton et al (1979) Bioorg. Chem 8, 351, (Fmoc-protected amino acids, protective acrylamide-silica gel based synthesis supports, deprotection with alkaline reagents, cleavage of peptides from supports with trifluoroacetic acid) have become popular. One characteristic that distinguishes the Merrifield and the Fmoc syntheses is that the former requires that reactions be carried out in a shaken reaction cell, whereas in the latter case the support can be packed into a column and reagents pumped through. The flow-through synthesis capabilities of the Fmoc method give it several advantages, which is one reason it has become increasingly popular in recent years.

Also in recent years there has been an increase in demand for small peptides of similar structure. One type of need is for epitope mapping of proteins, i.e., a search for the small regions (6–12 amino acids) of proteins that are antigenic sites for binding of antibodies; or immunogenic sites, which stimulate the immune response. Immunogenic peptides have the potential for use in making vaccines. One way to search for these sites in a protein containing, for example, 200 amino acids, is to synthesize a set of approximately 200 overlapping hexapeptides, each differing from its neighbor by a single amino acid. Other applications are the synthesis of analogs of a biologically active peptide, whether to find a more active peptide, or to determine which amino acids are responsible for activity, by systematic variation of the sequence. Synthesis of such large numbers of peptides one by one, such as those set forth below, even using a machine, is very time consuming.

| ABCDEFGHIJKLMNOP | ABCDEFG | ABCDEFG |
| ABCDE | XBCDEFG | AXCDEFG |
| BCDEF | AXCDEFG | AYCDEFG |
| CDEFG | ABXDEFG | AWCDEFG |
| DEFG | ABCXEFG | AZCDEFG |
| EFGHI | ABCDXFG | AQCDEFG |

There have been several methods and devices described to speed up this process. One of the first is the "teabag" method of Houghton (1985), Proc. Natl. Sci. USA 82, pg. 531 where synthesis is carried out on resins in small porous bags, which are soaked in solutions of the appropriate activated amino acid. Several bags can be placed in a single reaction vessel, and by proper "mixing and matching", several similar peptides can be synthesized (on a 50-100 umole scale) simultaneously. This process has not been automated, however. Another method is the "polypropylene peg method" of Geysen et al, (1985) Proc. Natl. Acad. Sci. USA 82, 178-182 wherein very small quantities ( 0.1 umole) of peptide are synthesized on small polypropylene rods by dipping the rods into the appropriate solutions. The quantities that can be made are very small, and the process is not automated. Other multiple peptide synthesis systems are DuPont's RaMPS system, which is manual, and the method of Schnorrenberg et al (1989), Tetrahedon 45, pgs. 7759-7764. The latter device uses a robot arm to deliver reagents to synthesis support resins in wells of a microtitre plate and is purported to be capable of synthesizing 96 peptides at once.

The various available methods can be classified somewhat arbitrarily, an "macroscale" (>10 umole), "microscale" ( 100 nmole) and "intermediate" (<100 nmole to 10 umole). Virtually all of the macroscale methods, many of which are automated, involve synthesis of peptides on resins and other types of beads. The microscale methods usually involve synthesis of peptides on surfaces such as polyethylene rods. Because of the small amounts of peptides synthesized, usually no attempt is made to isolate the peptide and the subsequent assay reactions involving the peptides are done directly on the surface, such as by binding antibodies to the surface. Macroscale synthesizers are very efficient but generally permit synthesis of only one peptide at a time. The primary problem with microscale methods is that they permit synthesis of only very small amounts of peptides or of peptides of very poor quality, e.g., 50% to 80% yields per cycle as compared with 99% for many macroscale synthesizers.

Accordingly, it would be desirable to provide a method and apparatus for producing a multiplicity of peptides in the micro to intermediate scale range which is rapid and effects high yields of peptide product.

SUMMARY OF THE INVENTION

In accordance with this invention, an apparatus is provided comprising two templates, each having a plurality of through-holes arranged in the same pattern. A chemically modified microporous membrane is positioned between the two templates so that the holes in a first template are aligned with the holes in the second template, and the exposed portion of the membrane between a set of mating holes is sealed from other sets of mating holes. A small hole is formed within each portion of the exposed membrane so that a differential pressure can be applied across the membrane without collapsing the membrane pores while effecting passage of liquid through the membrane. The membrane is chemically modified to bind to a protein moiety and, thus is useful in a variety of processes such as epitope mapping of antibodies, screening of cell surface receptor protein, structure function studies to develop bioactive peptides, e.g., hormones or the like. For example, when effecting epitope mapping by forming peptides from amino acid, with the apparatus of this invention, the reagents introduced onto the membrane would comprise, in series, a protected amino acid which binds to the membrane, a wash reagent to remove excess amino acid, a deprotecting reagent to deprotect the bound amino acid, a wash reagent to remove excess deprotecting agent, a second protected amino acid to react with the bound deprotected amino acid and, if desired, a capping reagent. A differential pressure is applied across the membrane after each step of reagent addition to the membrane in order to remove excess reagent from the membrane. The hole in the membrane prevents pore collapse so that the surface area of the membrane is retained during the peptide formation process.

DESCRIPTION OF SPECIFIC EMBODIMENTS

The apparatus of this invention includes a top template having a first set of holes, a bottom template having a second set of holes and a chemically modified membrane interposed between the two templates. The first set of holes and the second set of holes are in alignment with each other. Means are provided between the templates and in contact with the membranes to seal the areas of the membrane between the first set of holes and the second set of holes from the remainder of the membrane. The sealing is required in order to prevent crosstalk or leakage of reagents between exposed portions of the membrane. Each portion of the exposed membrane has a hole which extends through the membrane surface. The hole functions to permit the application of a differential pressure across the membrane while avoiding the collapse of the pores within the membrane. The use of a differential pressure across the membrane permits quick removal of the liquid diluent of a reagent from the membrane so that the next succeeding reagent can be applied to the membrane to effect the desired series of reactions.

Figure 5:
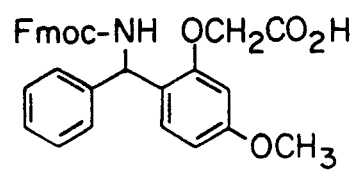
FIG. 5 shows the molecular structure of four linkers which generate peptides with C-terminal amides.
Figure 5:
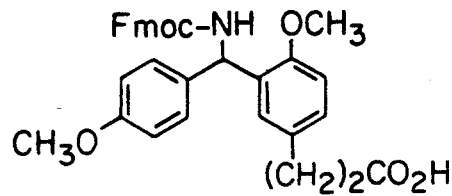
Figure 5:
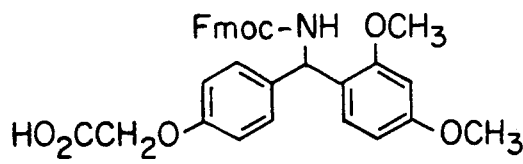
Figure 5:
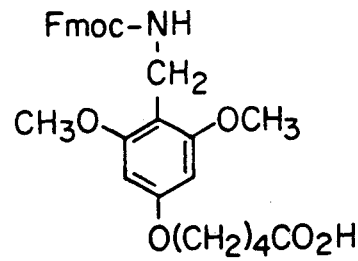
Figure 6:
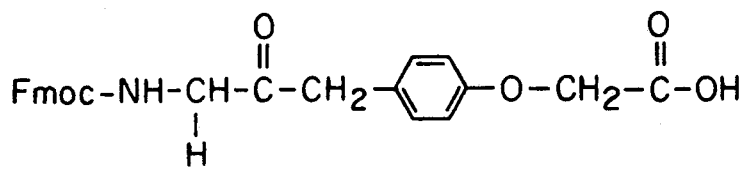
FIG. 6 shows the molecular structure of a linker which generates peptides with C-terminal carboxylic acids.

The porous membrane which is utilized in the present invention is chemically modified to react with amino acids in a manner such that peptides can be formed in situ on the membrane. Suitable membranes include polyolefin microporous membranes such as polyethylene or polypropylene functionalized with amino groups, carboxyl groups, alcohol groups or the like. When the peptide is synthesized by direct attachment of the amino acid carboxylic group to the membrane amino group, the peptide will be permanently linked to the membrane. Alternatively, a suitable linker can be attached to the amino or other functional group on the first amino acid to be reacted with the membrane substrate. Upon completion of the desired peptide formation, the peptide can be cleaved from the membrane in order to separate and recover the peptide. Some suitable linkers for reaction with the membrane amino groups include those shown in FIG. 5. In the case of these linkers, the linker is coupled to the membrane, the Fmoc protecting groups is removed and the polypeptide chain is then assembled on the exposed linker amino group. Cleavage of the peptide-linker bond with trifluoroacetic or other acid liberates a peptide with a carboxyl-terminal amide. Suitable amino acid-linker conjugates which can be coupled to the membrane amino groups include that shown in FIG. 6. In this case, cleavage of the peptide-linker bond with acid yields a peptide with a carboxyl-terminal carboxylic acid.

Figure 1:
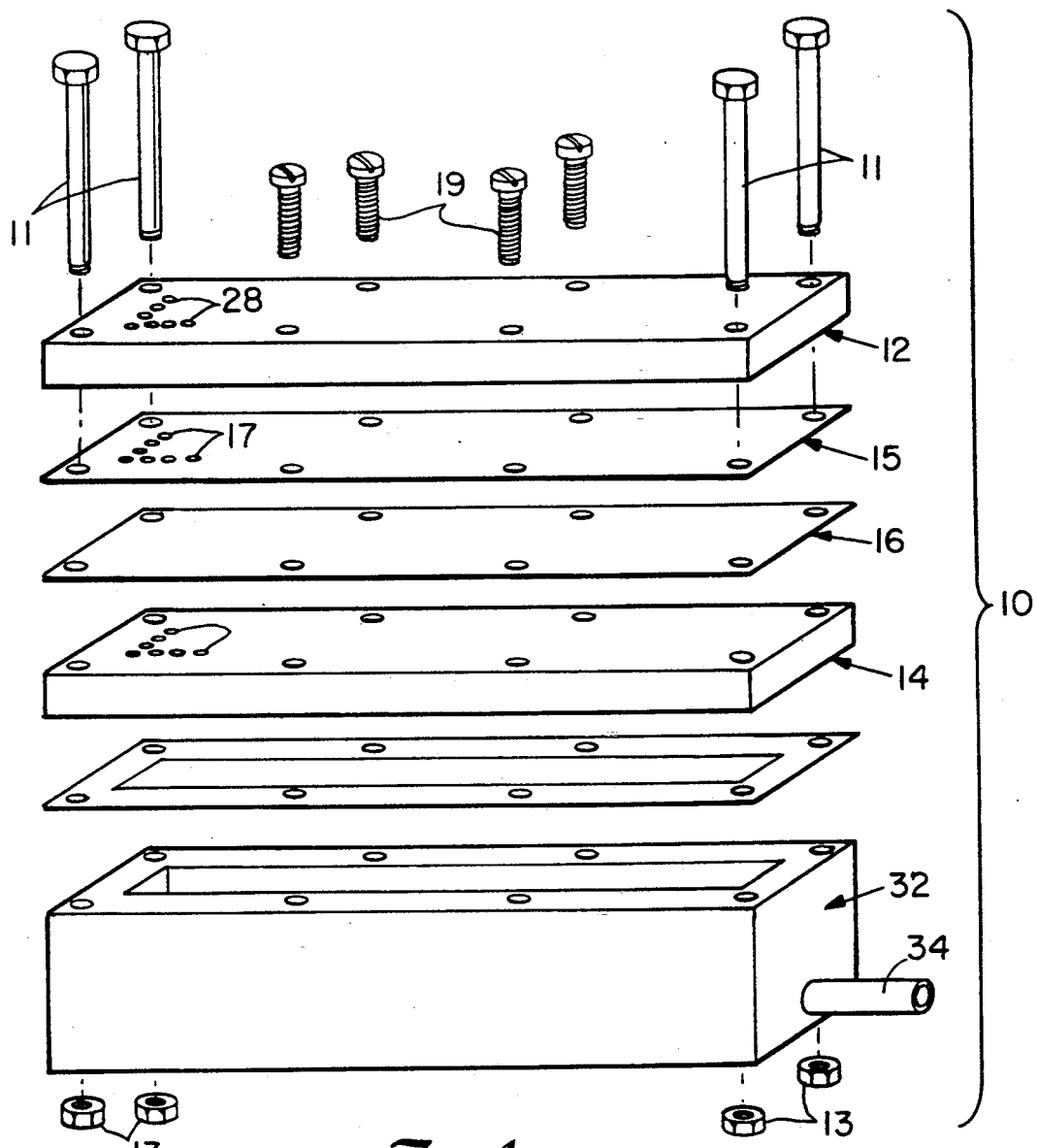
FIG. 1 is an isomeric exploded view of the apparatus of this invention
Figure 2:
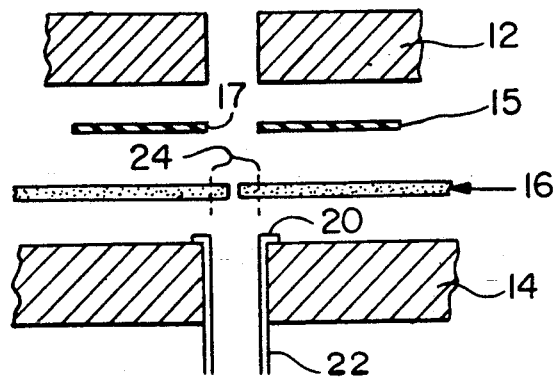
FIG. 2 is a cross-sectional view of a portion of the apparatus of FIG. 1.

The exposed portion of the membrane available for reaction are sealed from the remaining portion of the membrane by any convenient means. For example, an O-ring can be positioned about the periphery of each exposed portion of the membrane and a spout having flanges which cooperate with the O-ring can be inserted into the second set of holes to provide both sealing and direction of flow to the liquid being filtered. Alternatively, a rubber membrane having holes aligned with the templates can be inserted between the upper template and the synthesis membrane as shown in FIGS. 1 and 2. Other possibilities for isolating portions of membrane include the use of a template made of an inert, deformable material such as polyethylene, which combines the functions of the rubber gasket and spouts shown in FIGS. 1 and 2 or sealing portions of membrane to the bottoms of microtiter plate wells.

Referring to the FIGS. 1 and 2, the apparatus of this invention 10 includes a top template 12, a bottom template 14 and a porous membrane 16. The top and bottom templates 12 and 14 and clamped together by means of bolts 11 and nuts 13 or screws 19 during use so that the rubber gasket 15 having holes 17 and the flange 20, a centrifugal spout 22 when the apparatus 10 is bolted effectively seal the exposed portion of the membrane 24 from the remaining portion 26 of the membrane. The template 12 is provided with a first set of holes 28 and template 14 is provided with a second set of holes 30 which are aligned with each other so that a liquid reagent introduced into the first set of holes 28 can pass through the exposed portion of these membranes 24 and through the second set of holes to be discarded. In an important aspect of this invention, the exposed portion of the membrane 24 is provided with a through-hole 30. The through-hole 30 functions to prevent collapse of the exposed portion of the membrane when a pressure differential is applied across the membrane 24. A differential pressure across the membrane portion 24 can be effected conveniently by means of a plenum 32 bolted to the template 14 and which is connected to a source of a vacuum by means of conduit 34.

Figure 3:
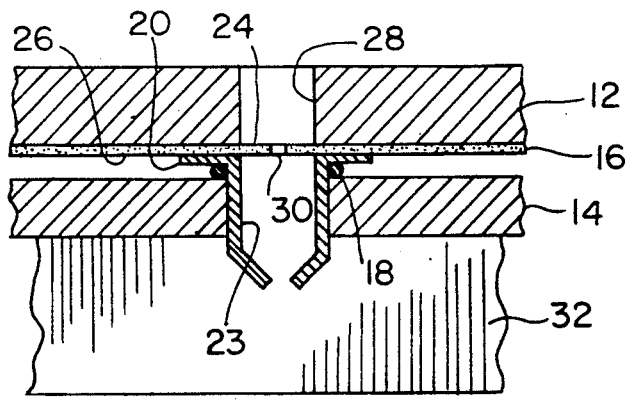
FIG. 3 is a cross-sectional view of an alternative embodiment of this invention.

As shown in FIG. 3, a sealing means is provided which includes an O-ring 18 which cooperates with the flange 20 of an Eppendorf tube 23. The exposed portion of the membrane 24 is provided with a through-hole 30.

Referring to FIG. 3, wherein like reference numerals as those in FIGS. 1 and 2 refer to the same element, and O-ring 18 rather than a rubber gasket 15 is utilized in conjunction with flange 20 to effect the desired seal.

When synthesis is complete, the sheet of membrane 16 is removed from the apparatus and protective groups are removed by treatment such as with trifluoroacetic acid, hydrofluoric acid or the like, using standard methods. This sheet can then be used directly for immunostaining, immunoluminescence detection or the like. If peptides are to be removed from the membrane, an acid-or otherwise labile linker must be added to the membrane before synthesis begins. Suitable acid labile linkers include those shown in FIGS. 5 and 6 (see also p. 8). After synthesis, individual spots are punched out of the membrane, and the peptide is released using trifluoroacetic or other cleavage reagents.

This device can be used to synthesize a variety of peptides including peptides containing 20 or more residues. Coupling yields average close to 99% per cycle. By contrast, the widely used Geysen method typically gives yields of 60–80% per cycle. Furthermore, the cycle time of this invention, typically is 30–60 minutes, compared with 18 hours for the Geysen method.

Figure 4:
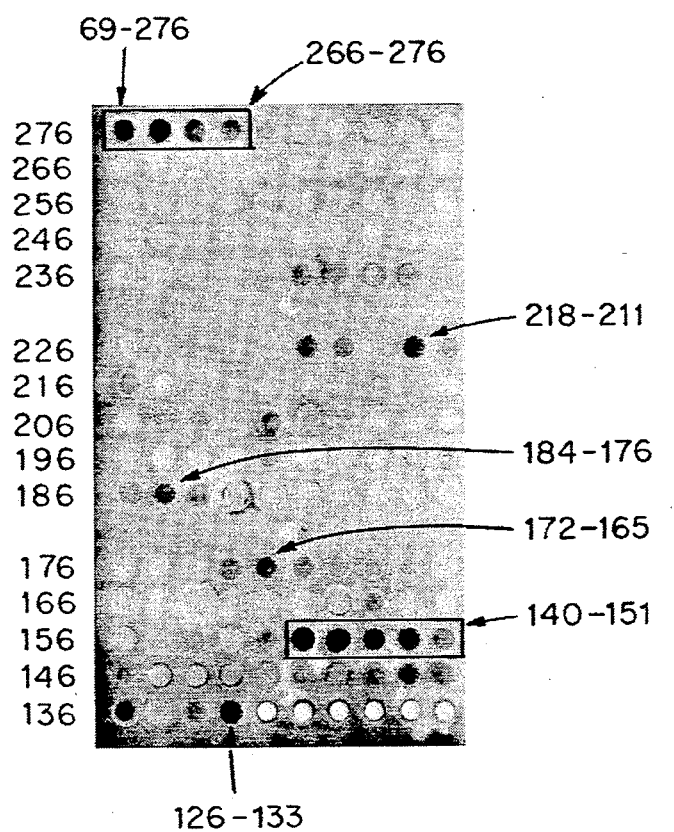
FIG. 4 illustrates the results obtained with the apparatus of this invention.

FIG. 4 shows the results of synthesis of 150 octapeptides from the carboxyl-terminal region of myelin proteolipid protein (PLP). The synthesis required only two days. After removal of protective groups, the membrane was incubated with polyclonal anti-PLP antiserum, followed by alkaline phosphatase conjugated anti-rabbit IgG and a substrate that yields an insoluble stain, or light, on hydrolysis by binding sites. In FIG. 4, the dark spots are epitopes, or antibody binding sites. Particularly noteworthy are the domains 266–276, known from earlier studies to be strongly antigenic, and 140–151, which is a known T-cell receptor site.

A typical peptide synthesis and detection protocol is as follows:

Peptide synthesis

1. Place a piece of synthesis membrane between the two templates of the synthesis device and tighten bolts.
2. Puncture the membrane using a syringe needle.
3. Wash the membrane by adding 75 ul of dimethylformamide (DMF, distilled from phosphorus pentoxide) to each well using an Eppendorf multipipetter. Apply vacuum to remove DMF. Repeat DMF wash 3 times.

Addition of linker. If linker is not needed, go directly to step 8.

4. Add 5–10 ul of 0.3M (Fmoc)-AM-linker/hydroxybenzotriazole (HOBt)/diisopropylcarodiimide (DIPCDI) mixture per well. Let stand at room temperature for 30 min.
5. Wash with DMF 5 times as in step 3.
6. Add 10–25 ul of 20% piperidine in DMF per well. Let stand 15 min. Drain off by vacuum.
7. Wash 10 times with DMF as in step 3.
8. Add 5–10 ul of 0.3M of Fmoc-amino acid-Opfp/HOBt to wells. Let stand for 30–60 min at room temperature.
9. Wash, deprotect with 20% piperidine and wash, as in steps 5–7.
10. Repeat as in steps 8 and 9 until the desired number of cycles has been completed.
11. When the synthesis has been completed, remove the membrane from the device, wash with DMF and then methanol and dry under vacuum.
12. Remove side-chain protecting groups with suitable trifluoroacetic acid cleavage reagent, e.g., TFA containing water, phenol, thiols, etc. as scavengers. [If a linker is present, individual spots are punched out and deprotection and cleavage are carried out individually.]
13. Wash membrane with methanol 3 times. Dry membrane under vacuum.

Binding of antibodies

14. Wash the membrane twice with TBS (20 mM Tris-Cl, 0.5M NaCl, pH 7.5.
15. Block the membrane for 0.5–1 hr. at room temperature with TBS-3% gelatin.
16. Wash membrane twice with TTBS (TBS-0.05% Tween-20)
17. Incubate membrane for 1–2 hr. at room temperature with antisera diluted in TTBS-1% gelatin.
18. Wash the membrane twice with TTBS.
19. Incubate the membrane for 1–2 hr. at room temperature in second antibody (e.g., alkaline phosphatase conjugated goat anti-rabbit IgG) diluted in TTBS-1% gelatin.
20. Wash twice with TTBS.
21. Wash twice with TBS.

Chemiluminescence detection (or go to step 26

22. Wash with Lumigen-PPD sustrate buffer (0.1M sodium bicarbonate, 1mM $MgCl_2$, pH 9.8.
23. Incubate membrane in Lumigen-PPD for 10 min.
24. Remove membrane, wrap with plastic film and expose to Kodak X-omat-AR film for 10–30 min. Develop film.
25. Wash membrane 3 times with 8M urea/0.1% sodium dodecyl sulfate, followed by 2 DMF washes and several TBS washes to remove antibodies and chemiluminescent substrate.

Detection by staining

26. Incubate membrane with substrate solution (e.g., 0.1 mg/ml of bromochloroindolyl phosphate (BCIP) and 0.3 mg/ml of nitroblue tetrazolium (NBT) until colors appear.

We claim:

1. Apparatus for effecting a plurality of independent chemical syntheses which comprises:
   a first template having a first set of through-holes positioned in a pattern,
   a second template having a second set of through-holes positioned in and aligned with said pattern,
   a chemically modified porous polymeric membrane positioned between said first and said second template,
   sealing means positioned between said first set of through-holes and second set of through-holes,
   means for applying differential pressure to effect fluid flow from said first set of holes to said second set of holes
   and means for preventing collapse of said membrane during application of said differential pressure,
   said chemically modified membrane having a first chemical moiety which permits covalent binding thereof with a second chemical moiety having a reactive carboxyl group.
2. The apparatus of claim 1 wherein said first set of through-holes and said second set of through-holes comprises a plurality of holes.
3. The apparatus of claim 1 wherein said chemical moiety includes a labile linker.
4. The apparatus of claim 2 wherein said chemical moiety includes an acid labile linker.
5. The apparatus of claim 1 which includes means for applying a differential pressure across said membrane.
6. The apparatus of claim 2 which includes means for applying a differential pressure across said membrane.
7. The apparatus of claim 3 which includes means for applying a differential pressure across said membrane.
8. The apparatus of claim 4 which includes means for applying a differential pressure across said membrane.

* * * * *